United States Patent [19]

Uhing et al.

[11] 4,000,190
[45] Dec. 28, 1976

[54] PROCESS FOR PREPARING ALKYL- AND ARYL PHOSPHONOTHIOIC DIHALIDES

[75] Inventors: Eugene H. Uhing, Ridgewood, N.J.; Arthur D. F. Toy, Stamford, Conn.

[73] Assignee: Stauffer Chemical Company, Westport, Conn.

[22] Filed: Feb. 10, 1975

[21] Appl. No.: 548,650

[52] U.S. Cl. .................................... 260/543 P
[51] Int. Cl.$^2$ .................................... C07F 9/42
[58] Field of Search .................... 260/543 P

[56] References Cited

UNITED STATES PATENTS 3,429,916    2/1969    Baker et al. .................. 260/543 P Primary Examiner—Norman Morgenstern

[57] ABSTRACT

Alkyl- and arylphosphonothioic dihalides are prepared by contacting a dialkyl or diaryl disulfide with phosphorus and phosphorus trihalide under at least autogenous pressure at a temperature of from about 200° C. to about 400° C. The compounds obtained are useful as constituents in insecticides, fungicides, pharmaceuticals and as intermediates in preparation of other organophosphorus compounds.

4 Claims, No Drawings

PROCESS FOR PREPARING ALKYL- AND ARYL PHOSPHONOTHIOIC DIHALIDES

BACKGROUND OF THE INVENTION

1. Field of the Invention

The present invention relates to a new and improved process for the preparation of alkyl- or arylphosphonothioic dihalides.

2. The Prior Art

Alkylphosphonothioic dihalides have been prepared in the prior art by reacting alkyl halides with phosphorus trihalides in the presence of aluminum chloride. The reaction proceeds at room temperature according to the formula set forth in Heuben-Weyl, *Methoden der Organis Chenchemie*, Volume 12, part 1 (1965) at page 396.

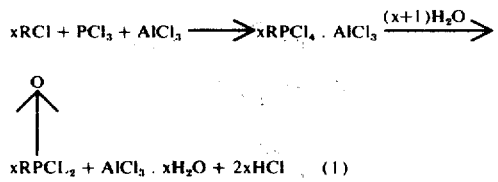

The Heuben-Weyl reference also notes that the reaction has been attempted in the absence of the aluminum chloride catalyst with little success. The alkylphosphonothioic dihalides are prepared by replacing the oxygen of the alkylphosphonic dihalide with sulfur as shown on page 553 of the Heuben-Weyl reference. The yields of the replacement reaction are limited to the yields obtained in the initial reaction forming the alkylphosphonic dihalide.

Other known methods of preparing alkylphosphonothioic dihalides are described in Journal of the American Chemical Society, 88 3041 (1966).

Alkyl- and arylphosphonothioic dihalides also can be prepared according to our U.S. Pat. No. 3,790,629 by reacting an aliphatic hydrocarbon with a pentavalent thiophosphorus compound having at least two halogens attached thereto under at least autogenous pressure at a temperature of from 200° C. to 450° C.

Cycloalkanephosphonothioic dichlorides have also been prepared by reacting a cycloalkene with thiophosphoryl chloride under irradiation with mercury lamps. Reaction times are long and low yields are reported (Angew, Chem. Internat. Edit., Vol. 9 (1970), No. 6 at p. 458).

Phosphorus trihalide and elemental phosphorus are wellknown and are readily available commercially.

SUMMARY OF THE INVENTION

In accordance with the present invention, there is provided a new method for preparing compounds of the formula:

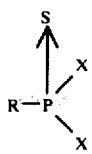
(I)

wherein R is a hydrocarbyl group consisting of hydrogen and carbon including $C_1$ to $C_{20}$ alkyl and the aryl (1 and 2 fused rings) substituted derivatives thereof, cycloalkyl of 5-6 carbons in the ring, aryl of up to 3 fused rings or biphenyl and the $C_1$-$C_4$ alkyl substituted derivatives of said cycloalkyl, aryl, or biphenyl and X is chlorine or bromine.

Typical alkyl groups include methyl, ethyl, n-propyl and isopropyl, n-butyl, isobutyl, tert-butyl, pentyl, hexyl, heptyl, octyl, nonyl, decyl, dodecyl, tetradecyl, hexadecyl, octadecyl and eicosyl. Some suitable aralkyl groups are phenylmethyl, phenylethyl, phenylbutyl, phenyloctyl, phenylhexadecyl, and the corresponding naphthyl derivatives. Ring systems wherein R is cycloalkyl having 5–6 carbons in the ring are illustrated by cyclopentyl and cyclohexyl and their derivatives.

Examples of aryl and substituted aryl groups include phenyl, methylphenyl, ethylphenyl, propylphenyl, and butylphenyl, naphthyl, methylnaphthyl, ethylnaphthyl, propylnaphthyl, butylnaphthyl, anthryl, methylanthryl, propylanthryl, butylanthryl, as well as dimethylphenyl, dimethylnaphthyl, diethylanthryl, and the like. Any of said groups can contain one or more alkyl radicals and any isomeric form of said groups can be used.

Biphenyl R groups include the $C_1$ to $C_4$ alkyl substituted derivatives such as methylbiphenyl and ditolyl. There can be one or more substituents as desired and said substituents can be in any isomeric position desired. The R groups also can be connected to the phosphorus at any isomeric position.

With respect to X, chlorine is preferred over bromine as it is inexpensive and reacts readily. Bromine, however, can be used if it is desired to have bromine in the final compound. Also, bromine is useful in the preparation of bromine containing intermediates for flame retardant compounds.

The method of the present invention comprises contacting a dialkyl or diaryl disulfide reactant of the general formula:

RSSR (II)

wherein R is as defined above, with phosphorus and phosphorus trihalide reactants of the formula:

$PX_3$ (III)

wherein X is as defined above.

The following equation (2) is representative of the reaction:

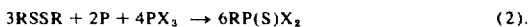

$3RSSR + 2P + 4PX_3 \rightarrow 6RP(S)X_2$ (2).

Representative compounds within the formula (II) include dimethyl disulfide, dipropyl disulfide, dibutyl disulfide, dioctyl disulfide, didecyl disulfide, didodecyl disulfide, dihexadecyl disulfide, dioctadecyl disulfide, dieicosyl disulfide, dicyclopentyl disulfide, dicyclohexyl disulfide, dibenzyl disulfide, ditolyl disulfide, diethylbenzyl disulfide, dipropylbenzyl disulfide, dibutylbenzyl disulfide, dinaphthyl disulfide, dimethylnaphthyl disulfide, diethylnaphthyl disulfide, dimethylanthryl disulfide, dibutylanthryl disulfide and the like.

The foregoing compounds are given as illustrative and are in no way considered to be totally inclusive of all of the dialkyl and diaryl disulfides which can be used in the method of the present invention. Preparation of such disulfides is described in Synthetic Organic Chemistry by R. B. Wagner and H. D. Zook (Wiley, 1953) at Chapter 33.

Compounds of the formula (III) are phosphorus trichloride and phosphorus tribromide.

Reactants utilized in the process of the present invention can be employed in stoichiometric amounts, although an excess of any of the reactants can be used if desired.

The process of the present invention is carried out at elevated temperatures and at least at autogenous pressure and generally at a pressure of between about 1 and 300 atmospheres. Temperatures of from about 200° C. to about 400° C. can be used although temperatures of from about 250° C. to about 375° C. are preferred for the reaction to proceed to completion in a reasonable time.

Reaction times can vary over relatively wide ranges and can easily be determined by one skilled in the art. Factors affecting reaction time include reactivity of the reactants and temperature. For example, reactivity of dialkyl disulfides increases with chain length and reaction time therefore decreases accordingly. Reaction time generally decreases with increases in reaction temperature. Typical reaction times are from about 1 to about 24 hours.

The process of the present invention requires no separate catalyst in order to effect reaction.

The process of the present invention can conveniently be effected by introducing the individual reactants into a reaction zone capable of withstanding elevated pressure, such as a metal bomb, autoclave, or other pressure vessel, and carrying out the reaction under at least the autogenous pressure developed by the reactants at the reaction temperature. An agitation means should be provided for said reaction zone. The reaction can be carried out in a continuous or batchwise system as desired.

The products of the reaction are purified by conventional methods such as by fractional distillation of liquids and sublimation, crystallization or extraction of solid products.

The identification of products is achieved by conventional methods, such as elemental analysis, and gas chromatography for purity and mass spectrometer and nuclear magnetic resonance and infrared analysis to establish structure.

Illustrative of the compounds which can be prepared by the method of the present invention are:

Alkyl:
$CH_3P(S)Cl_2$
$CH_3P(S)Br_2$
$C_2H_5P(S)Cl_2$
$C_2H_5P(S)Br_2$
$C_3H_7P(S)Cl_2$
$C_4H_9P(S)Cl_2$
$C_4H_9P(S)Br_2$
$C_5H_{11}P(S)Cl_2$
$C_8H_{17}P(S)Cl_2$
$C_8H_{17}P(S)Br_2$
$C_{18}H_{37}P(S)Cl_2$

CYCLIC COMPOUNDS

Aromatic

Benzene:

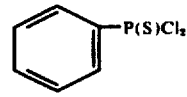

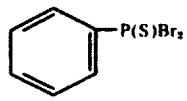

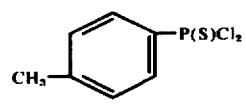

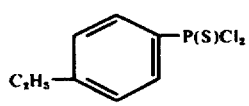

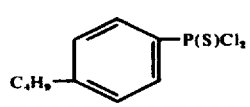

Naphthalene:

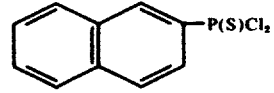

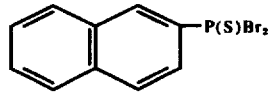

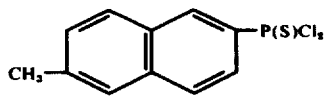

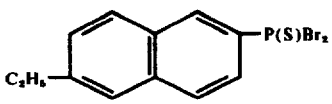

Anthracene:

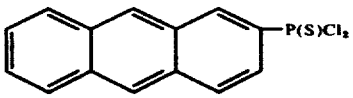

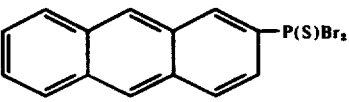

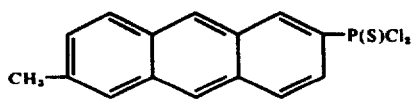

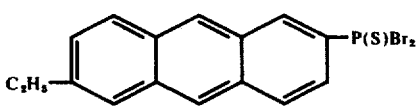

CYCLIC COMPOUNDS-continued

Biphenyl:

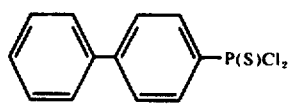

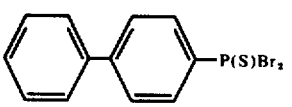

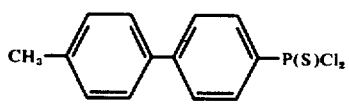

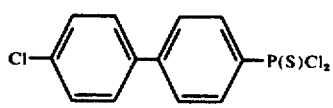

Cycloalkyl

5 Membered carbon ring:

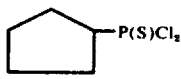

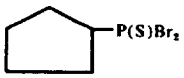

6 Membered carbon ring:

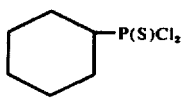

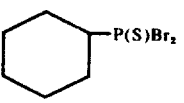

The products of the present invention are dihalides of pentavalent phosphorus and, therefore, can be subject to all the known reactions which such compounds undergo. Said products can be used to make insecticides as illustrated by the process for making O-ethyl O-paranitrophenyl phenylphosphonothioate as per the following illustrative reaction scheme:

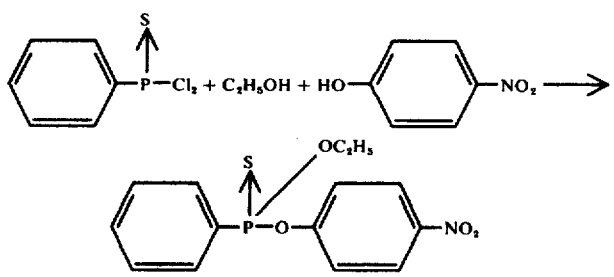

and for making O-ethyl S-phenyl ethylphosphonothioate as per the following illustrative reaction scheme:

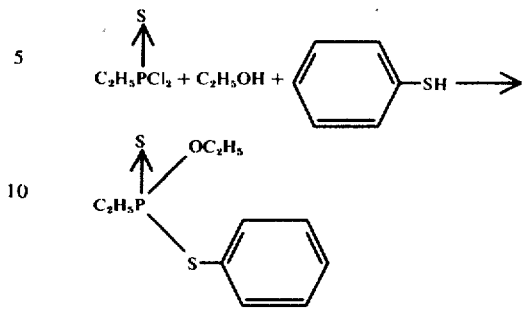

Other uses of the products of the present invention as constituents in insecticides, fungicides, pharmaceuticals, and as intermediates in preparation of other organophosphorus compounds are known.

EXAMPLE I

In a 300 milliliter 316 stainless steel autoclave rated at 5,000 pounds per square inch gauge are placed 40.5 grams $(C_2H_5S)_2$ (0.33 mole); 7.2 grams yellow phosphorus (0.23 gram atoms) and 64.0 grams $PCl_3$ (0.465 mole). The autoclave is closed and heated to effect reaction. Heat of reaction is maintained at 300° C. for 12 hours. The autoclave is opened and the contents are distilled. The distilled yield of $C_2H_5P(S)Cl_2$ is 51.0 grams or 47.5 percent, as identified by gas-liquid chromatography. Thirty-one grams of a high boiling product and 11 grams of a nondistillable residue also are produced.

EXAMPLE II

In a 300 milliliter 316 stainless steel autoclave rated at 5,000 pounds per square inch gauge are placed 28.3 grams $(CH_3S)_2$ (0.3 mole); 58.4 grams $PCl_3$ (0.42 mole) and 6.2 grams yellow phosphorus (0.2 gram atoms). The autoclave is closed and heated to effect reaction at 340° C. for 12 hours. After cooling and venting the autoclave, the yield of crude product weighs 82.2 grams.

The crude product has the following analysis by gas-liquid chromatography with internal standard:

| Compound | Weight % |
|---|---|
| $PCl_3$ | 10.2 |
| $P(S)Cl_3$ | 2.8 |
| $CH_3P(S)Cl_2$ | 65.1 |
| $(CH_3)_2P(S)Cl$ | 17.5 |
| low boiling components | 2.5 |
| high boiling components | 1.9 |

The crude product also is analyzed by [31]phosphorus nuclear magnetic resonance to confirm the identity of the phosphorus containing compounds.

Having set forth the general nature and some examples of the present invention, the scope is now particularly set forth in the appended claims.

What is claimed is:

1. A method of preparing compounds of the formula:

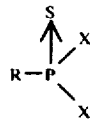 (I)

wherein R is a hydrocarbyl group selected from the group consisting of $C_1$ to $C_{20}$ alkyl; the aryl substituted derivatives thereof, said aryl having 1 or 2 fused rings; cycloalkyl of 5-6 carbons in the ring; aryl of up to 3 fused rings; biphenyl and the $C_1$-$C_4$ alkyl substituted derivatives of said cycloalkyl, aryl and biphenyl and X is selected from the group consisting of chlorine and bromine, comprising contacting under at least an autogenous pressure at a temperature of from about 200° C. to about 400° C. a reactant of the formula:

RSSR  (II)

wherein R is as defined above with a phosphorus trihalide of the formula:

$PX_3$  (III)

wherein X is as defined above, and phosphorus.

2. The method of claim 1 wherein R is alkyl selected from the group consisting of methyl, ethyl, n-propyl, isopropyl, n-butyl, isobutyl, tertbutyl, pentyl, hexyl, heptyl, octyl, nonyl, decyl, dodecyl, tetradecyl, hexadecyl, octadecyl and eicosyl.

3. The method of claim 1 wherein R is aralkyl selected from the group consisting of phenylmethyl, phenylethyl, phenylbutyl, phenyloctyl, phenylhexadecyl, and the corresponding naphthyl derivatives.

4. The method of claim 1 wherein R is aryl selected from the group consisting of phenyl, methylphenyl, ethylphenyl, propylphenyl, and butylphenyl, naphthyl, methylnaphthyl, ethylnaphthyl, propylnaphthyl, butylnaphthyl, anthryl, methylanthryl, propylanthryl, butylanthryl, as well as dimethylphenyl, dimethylnaphthyl, diethylanthryl biphenyl and derivatives thereof.

* * * * *